US009408866B2

(12) United States Patent
Thomas et al.

(10) Patent No.: US 9,408,866 B2
(45) Date of Patent: Aug. 9, 2016

(54) METHOD FOR DETOXIFICATION OR MEASUREMENT OF AT LEAST ONE COMPOUND OR AT LEAST ONE FLUID IN A HOST BODY

(71) Applicant: NIVA, Oslo (NO)

(72) Inventors: Kevin V. Thomas, Kolsas (NO); Katherine Hailey Langford, Kolsas (NO); Alfhild Kringstad, Haslum (NO); Ian John Allan, Slemmestad (NO)

(73) Assignee: NIVA, Oslo (NO)

( * ) Notice: Subject to any disclaimer, the term of this patent is extended or adjusted under 35 U.S.C. 154(b) by 0 days.

(21) Appl. No.: 14/397,124

(22) PCT Filed: Apr. 25, 2013

(86) PCT No.: PCT/NO2013/050074
§ 371 (c)(1),
(2) Date: Oct. 24, 2014

(87) PCT Pub. No.: WO2013/162382
PCT Pub. Date: Oct. 31, 2013

(65) Prior Publication Data
US 2015/0132245 A1 May 14, 2015

(30) Foreign Application Priority Data
Apr. 26, 2012 (NO) .................................. 20120485

(51) Int. Cl.
*A61F 2/00* (2006.01)
*A61K 31/74* (2006.01)
*A61K 31/80* (2006.01)
*A61K 9/00* (2006.01)
*G01N 33/52* (2006.01)
*G01N 30/88* (2006.01)

(52) U.S. Cl.
CPC ............... *A61K 31/74* (2013.01); *A61K 9/0024* (2013.01); *A61K 31/80* (2013.01); *G01N 33/521* (2013.01); *G01N 2030/8813* (2013.01); *G01N 2560/00* (2013.01)

(58) Field of Classification Search
None
See application file for complete search history.

(56) References Cited

U.S. PATENT DOCUMENTS 6,007,498 A 12/1999 Buck et al.
2002/0128579 A1 9/2002 Church 2006/0070950 A1 4/2006 Rasmussen et al.
2007/0090058 A1 4/2007 Southard
2009/0118562 A1 5/2009 Cole et al.

FOREIGN PATENT DOCUMENTS

| CN | 101139411 A | 3/2008 |
|---|---|---|
| EP | 0781787 B1 | 9/2000 |
| FR | 2695208 A1 | 3/1994 |
| FR | 2917402 | 12/2008 |
| GB | 2113226 A | 8/1983 |
| GB | 2466041 A | 6/2010 |
| JP | 2008080102 A | 4/2008 |
| WO | 2005024389 A1 | 3/2005 |
| WO | 2009123660 A2 | 10/2009 |
| WO | 2010086985 A1 | 8/2010 |

OTHER PUBLICATIONS

Extended European Search report for 13781742.5, Completed Oct. 15, 2015.
Kossovsky et al. "⊞ A Pathophysiological Examination of the Biophysics and Bioreactivity of Silicone Breast Implants", Aug. 1, 1994.
Baltussen et al. "Stir Bar Sorptive Extraction (SBSE), a Novel Extraction Technique for Aqueous Samples—Theory and Principles", Presented Jun. 20, 1999.
Salipira et al. "Carbon nanotubes and cyclodextrin polymers for removing organic pollutants from water", Environmental Chemistry Letters, Feb. 2007, vol. 5, Issue 1, pp. 13-17.
Search report Norway Patent Application No. 20120485, reported Nov. 7, 2012.
International Search Report and Written Opinion for PCT:NO2013:050074, mailed Sepetember 13, 2013.
International Preliminary Report on Patentability for PCT:NO2013:050074, completed Aug. 8, 2014.
Yantasee, et. al "Functionalized Nanoporous Silica for the Removal of Heavy Metals from Biological Systems—Adsorption and Application"; Appl Matter interfaces, Oct. 2, 2010(10) 2749-2758.

*Primary Examiner* — Susan Tran
(74) *Attorney, Agent, or Firm* — Brinks Gilson & Lione

(57) ABSTRACT

The present invention comprises a method for detoxification or measurement of the concentration of at least one compound in a host body, wherein said host body comprises a sorption material of at least one phase over a certain period of time, where sorption of said at least one compound in at least one phase of said sorption material is effected and the content of the at least one compound in said sorption material is optionally analyzed. Use of a sorption material for providing an estimate of the concentration of compounds present in a host body, use of a sorption material for detoxification and sorption material for diagnostic use is also comprised in the present application.

19 Claims, 1 Drawing Sheet

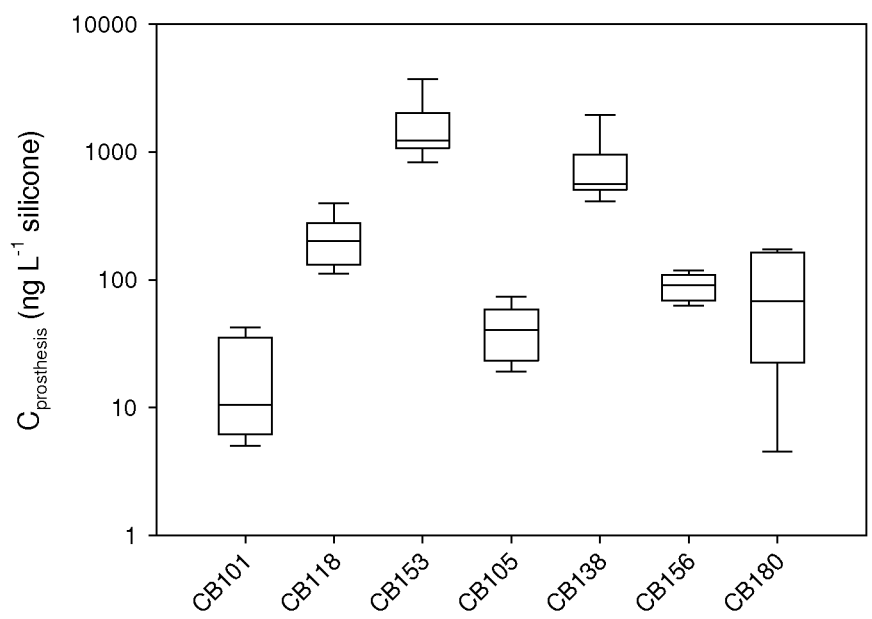

METHOD FOR DETOXIFICATION OR MEASUREMENT OF AT LEAST ONE COMPOUND OR AT LEAST ONE FLUID IN A HOST BODY

RELATED APPLICATIONS

This application claims the benefit under 35 U.S.C. §371 of International Patent Application No. PCT/NO2013/050074, having an international filing date of Apr. 25, 2013, which claims priority to Norwegian Application No. 20120485, filed Apr. 26, 2012, the contents of both of which are incorporated herein by reference in their entirety.

INTRODUCTION

The present invention relates to a method for the detoxification or measurement of at least one compound or at least one fluid in a host body. In addition a method for measurement of at least one compound in a sorption material for providing an estimate of the concentration of said compound(s) present in a host body is also part of the present invention.

Furthermore, use of a sorption material for providing an estimate of the concentration of compounds present in a host body is disclosed herein. Use of a sorption material for detoxification and sorption material for diagnostic use is also disclosed in the present application.

BACKGROUND OF THE INVENTION

The assessment of the risk and hazard posed to humans by the wide variety of chemicals released to the environment relies on measurements of contaminant levels in sources and environmental media, and increasingly on the use of bio monitoring tools. Recently, the World Health Organization and the Stockholm Convention joined forces to coordinate a survey of human exposure to persistent organic pollutants (POPs) through monitoring of milk and blood. Chemical risk management is undertaken by controlling and reducing the amount of substances we are exposed to in everyday life. Sources of contaminants include for example water, air, food, soil, dust, personal care products, or house furniture with three routes of entry, ingestion, inhalation, and dermal contact.

Bio monitoring should be understood as the measurement of the content or concentration of a compound, a chemical, a metabolite of the chemical of interest or a reaction product in human tissue, matrix or sorption material.

W. Yantasee et al., "Functionalized Nanoporous Silica for the Removal of Heavy Metals from Biological Systems: Adsorption and Application", Appl Matter interfaces, 2010 Oct. 2 (10, pp. 2749-2758 refers to the use of several types of silica based materials as sorbents to capture heavy metals. In particular, functionalized nanoporous silica, often referred to as self-assembled monolayers on mesoporous supports (SAMMS), are used to remove selected heavy metals from biological solutions like blood and urine.

US 2009/0118562A1 refers to sorptive sheet materials in which finely divided nanocrystalline particles that react with a variety of chemicals and/or biological agents are dispersed. The sheet material can be used in a wide variety of applications including protective garments, human remain pouches, filtration equipment, absorptive pads and wipes and the like. The sorptive material is capable of sorbing and neutralizing or chemically altering undesirable substances such as toxic agents like chemical and biological agents, odors and odor-causing compounds, and toxic industrial chemicals. In one embodiment US 2009/0118562A1 discloses removal of chemicals caused by chemical/biological weapons from a body being exposed to such agents by placing the body into a pouch comprising the sorptive material.

While it may be appropriate to measure contaminant levels in target organs (e.g. liver or brain), this can in most cases only be undertaken with diseased patients. It is an object of the present invention to obtain alternative materials for detoxification or measurement such as sorption materials or matrices in order to measure chemicals in living organisms. The said chemicals are hydrophobic compounds accumulating in the body; i.e. bio accumulating compounds/bio transforming compounds.

An understanding of the speciation of a chemical in the body is needed to determine which alternative matrix is best suited for bio monitoring. The speciation mentioned in the present invention should be understood as i.a. the partitioning of contaminant between different phases.

A host body should be understood as a human or non-human organism.

A sorption material should be understood as a device comprising one or more phases wherein at least one of the said phases comprise one or more sorbent possessing the ability of sorption of chemicals accumulated in the body.

Lipophilic and persistent organic substances (e.g. PCBs) commonly stored in lipids can be measured in matrices in which their concentrations can equilibrate with concentrations in lipids. These include blood, milk or adipose tissue. The establishing of equilibrium between contaminant concentrations in various matrices or tissues in the body is expected to be a rapid process.

In the present invention, the potential of explanted silicone breast prostheses as a sorption material for detoxification or measurement of compounds in a host body has surprisingly been found as a successful method for routine monitoring of among others lipophilic organic compounds in living organisms. The expression explanted silicone prostheses should be understood as prostheses which have previously been implanted into a host body for a certain period of time and thereafter removed from said host body. In the present disclosure the inventors have found that among others an implant, prosthesis and/or an adhesive bandage as a sorption material will accumulate hydrophobic compounds from their surroundings. Further, concentration of the compound(s) in the sorption material has been found to reach equilibrium relatively rapidly with those in the body.

SUMMARY OF THE INVENTION

The present invention is conceived to solve or at least alleviate the problems identified above.

A first aspect of the present invention relates to a method for detoxification or measurement of the concentration of at least one compound in a host body, wherein said host body comprises a sorption material of at least one phase over a certain period of time, where sorption of said at least one compound in at least one phase of said sorption material is effected and the content of the at least one compound in said sorption material is optionally analysed.

By "sorption" in the present invention is meant adsorption and/or absorption.

In one embodiment the sorption material is optionally removed from the host body prior to being optionally analysed.

Another aspect of the present invention comprises a method for detoxification or measurement of the concentration of at least one fluid in a host body, wherein said host body comprises a sorption material of at least one phase, wherein sorption of said at least one compound in at least one phase of said sorption material is effected and the content of the at least one compound in said sorption material is optionally analysed.

In a preferred embodiment of the present invention it is provided a method for detoxification of at least one hydrophobic compound or fluid in a host body, wherein said host body comprises a sorption material of at least one phase over a certain period of time, where sorption of said at least one compound or fluid in at least one phase of said sorption material is effected, wherein said sorption material is an implant or prosthesis which previously has been implanted in a host body for a certain period of time, or an adhesive sorption material which previously has been present on the surface of a host body for a certain period of time, and thereafter the sorption material is removed from the host body in order to achieve detoxification.

In another preferred embodiment of the present invention it is provided a method for measurement of the concentration of at least one hydrophobic compound or fluid in a host body, wherein said host body comprises a sorption material of at least one phase, wherein sorption of said at least one compound or fluid in at least one phase of said sorption material is effected and the content of the at least one compound or fluid in said sorption material is analysed, wherein the sorption material is an implant, a breast implant, a prosthesis and/or an adhesive bandage.

In a further aspect the present invention comprises a method for measurement of the concentration of at least one compound in a sorption material for providing an estimate of the concentration of said compound(s) present in a host body in which the sorption material previously has been implanted for a certain period of time, said method comprising the following steps:

bringing said sorption material in contact with at least one solvent, analyzing extracted compounds.

In an aspect of the present invention comprises a method for detoxification or measurement of the concentration of at least one compound in a host body, wherein said host body comprises a sorption material of at least two phases over a certain period of time, wherein sorption of said at least one compound in at least one phase of said sorption material is effected and the content of the at least one compound in said sorption material is optionally analysed.

Another aspect of the present invention comprises a method for detoxification or measurement the concentration of at least one fluid in a host body, wherein said host body comprises a sorption material of at least two phases, wherein sorption of said at least one compound in at least one phase of said sorption material is effected and the content of the at least one compound in said sorption material is optionally analysed.

In addition an acid clean up is performed optionally prior to analyzing the extracted compounds. An optional acid clean up according to the present invention is performed when the sorption material is among others silicone. Strong acids tend to hydrolyze silicones such as silicone and siloxane compounds into small(er) oligomers. Silicone oligomers can vary across a wide range of molecular size. Most of them are relatively insoluble in water.

The sorption material after being brought in contact with at least one solvent is brought to a temperature in at least one of the selected ranges: −10° C. to +10° C., −5° C. to 5° C., −5° C. to 0° C., 0° C. to 5° C. Said solvent extract is combined with water to precipitate oligomers.

The extracted compounds are analyzed using one of the following methods: gas chromatography, liquid chromatography or mass spectrometric methods for detection and quantification. Gas chromatography and liquid chromatography are preferably chosen for analyzing organics. Further, mass spectrometric methods such as ICP-AES and ICP-MS are chosen for analyzing metals and radio nuclides.

In one embodiment the sorption material according to the present invention comprises one phase. In another embodiment the sorption material comprises two phases wherein one phase constitute the inner phase being a gel and the second phase constitute the outer phase being another gel. Said outer phase being another gel or another material may constitute a textured and more solid outer layer. Further according to the present invention the sorption material may include several phases in which each constitute different phases. The term "phase" according to the present invention would be understood by the skilled person. The sorption material relating to the present invention comprises at least one phase constituting at least one of the following: gels, polymers, polydimethylsiloxane, ethylene vinyl acetate, biocompatible and medical grade polymers, rubbery polymers, silicone, additives such as activated carbon, resins, molecularly imprinted polymers (MIPs), nanoparticles, nanomaterials. Furthermore, said at least one phase may comprise resins such as XAD, ion exchange and/or chelating agents.

The sorption material according to the present invention possesses the ability of sorption of at least one of the following compounds:

any organic molecule, any inorganic molecule or organo metallic such as e.g. methyl mercury. In a preferred method of the present invention the sorption material possesses the ability of sorption of at least one of the following compounds: dichlorodiphenyltrichloroethane isomers (DDT) and metabolites, hexachlorobenzene (HCB), octachlorostyrene (OCS), pentachlorobenzene (PeCB), polychlorinated biphenyl congeners (209 PCB congeners) and brominated diphenyl ethers (209 PBDE congeners), nonpolar degradation products thereof such as hydroxyl-BDEs, polycyclic aromatic hydrocarbons and metabolites thereof, metabolites of PCBs/PBDEs, hexabromocyclododecane, in other words any neutral non-ionised substances comprising an octanol-water partition coefficient (log $K_{ow}$)>3.

The present invention comprises use of a sorption material for providing an estimate of the concentration of compounds present in a host body.

In addition the present invention comprises use of a sorption material for detecting compounds present in a host body.

A further advantage of the present invention is the use of the sorption material for detecting compounds present in a host body wherein said sorption material being an implant or prosthesis which previously has been implanted in a host body for a certain period of time. In the present invention it should be understood that a certain period of time comprises at least one of the following: 3 hours, 4, hours, 5 hours, 6-10 hours, 11-15 hours, 16-20 hours, 1 day, 2 days, 1-2 days, 3-5 days, 6-10 days, 1 month, 2 months, 3-6 months, 7-12 months, 18 months, 2-5 years, 6-10 years, 11-15 years, 16-20 years, 21-30 years, 31-40 years.

According to the present invention said sorption material may be an adhesive sorption material which has been present on the surface of a host body for a certain period of time.

An embodiment comprises sorption material for use in detoxification of a host body. Furthermore, said detoxification involves sorption of compounds present in a host body, i.e. bio accumulating compounds. In addition said sorption material is inserted into the host body and kept there for a certain period of time, and thereafter removed from the host body in order to achieve detoxification.

In one embodiment the sorption material for use in detoxification of a host body may according to the present invention be placed on the surface of the host body and kept there for a certain period of time, and thereafter removed from the host body in order to achieve detoxification. A certain period of time comprises at least one of the following: 3 hours, 4, hours, 5 hours, 6-10 hours, 11-15 hours, 16-20 hours, 1 day, 2 days, 1-2 days, 3-5 days, 6-10 days, 1 month, 2 months, 3-6 months, 7-12 months, 18 months, 2-5 years, 6-10 years, 11-15 years, 16-20 years, 21-30 years, 31-40 years.

An adhesive sorption material is useful to wear for instance when staying in areas of high pollution e.g. PCBs pollution. Adhesive sorption material is also useful for pregnant and breast-feeding women in order to avoid accumulation of toxic compounds in the body which are transferred to the embryo and/or infant.

The adhesive sorption material should preferably be placed on an area of the body excepted to be contaminated. Typically, this is an area of adipose tissue.

In a preferred embodiment of the present invention the use of a sorption material for detoxification of hydrophobic compounds present in a host body, wherein said sorption material is
  an implant or prosthesis which previously has been implanted in a host body for a certain period of time, or
  an adhesive sorption material which previously has been present on the surface of a host body for a certain period of time,
and thereafter the sorption material is removed from the host body in order to achieve detoxification, is provided.

In another preferred embodiment of the present invention the use of a sorption material for providing an estimate of the concentration of hydrophobic compounds present in a host body, wherein said sorption material is
  an implant or prosthesis which previously has been implanted in a host body for a certain period of time, or
  an adhesive sorption material which previously has been present on the surface of a host body for a certain period of time,
is provided.

The sorption material has a preferred sorption for compounds not naturally present in a host body. The sorption material comprises at least one phase comprising at least one of the following: gels, polymers, polydimethylsiloxane, ethylene vinyl acetate, biocompatible and medical grade polymers, rubbery polymers, silicone, additives such as activated carbon, resins, molecularly imprinted polymer (MIPs), nanoparticles, nanomaterials. The sorption material possesses the ability of sorption of at least one of the following bio accumulated compounds: any organic molecule, any inorganic molecule, methyl mercury.

The sorption material according to the present invention possesses the ability of sorption of at least one of the following compounds: dichlorodiphenyltrichloroethane isomers (DDT) and metabolites, hexachlorobenzene (HCB), octachlorostyrene (OCS), pentachlorobenzene (PeCB), polychlorinated biphenyl congeners (209 PCB congeners) and brominated diphenyl ethers (209 PBDE congeners), nonpolar degradation products thereof such as hydroxyl-BDEs, polycyclic aromatic hydrocarbons and metabolites thereof, metabolites of PCBs/PBDEs, hexabromocyclododecane, in other words any neutral non-ionised substances comprising an octanol-water partition coefficient (log $K_{ow}$)>3.

Said sorption material according to the present invention comprises at least one phase.

The sorption material according to the present invention is an implant, a breast implant, prosthesis and/or an adhesive bandage.

In one embodiment the invention provides a sorption material wherein the sorption material is an implant, a breast implant, prosthesis and/or an adhesive bandage, for use in detoxification of at least one hydrophobic compound or fluid in a host body.

The present invention comprises sorption material for diagnostic use.

In one embodiment the present invention provides a sorption material wherein the sorption material is an implant, a breast implant, prosthesis and/or an adhesive bandage for diagnostic use.

In one embodiment the sorption material has a preferred sorption for compounds naturally present in a host body.

SUMMARY OF THE DRAWING

FIG. 1 illustrates box plot of concentration range, median, max/min concentration of PCBs, OCs and PBDEs in human prostheses.

DETAILED DESCRIPTION

The object of the present invention is the detoxification or measurement of chemical contaminants such as persistent organic pollutants, metals, or radionuclides in living organisms. Surprisingly the inventors have observed that implants need suitable materials in order to detoxify or measure POP's in living organisms. Thus the present inventors came up with the idea that silicone implants could be used to measure POP's in order to investigate contaminants present in living organisms further. Surprisingly the inventors were able to prove a number of contaminants in breast implants which have previously been implanted.

Further it seems that prior art methods lack the presence of blank samples. The present invention is a reliable method with the basis in blank samples since it is possible to measure the difference between the blank sample and the sample.

Challenges associated with more conventional bio monitoring matrices such as blood, serum, adipose tissue or milk include the availability of (field)-blanks to be treated in a similar way to real samples and adequate material for the production of spiked samples to be processed with each extraction batches. For prostheses as a sampling tool, the availability of blanks from clinics or directly from the manufacturer enables us improved control over extraction and analysis. The performance of the prosthesis extraction method was evaluated through recoveries from spiked samples and levels measured in blank prostheses. Blank prostheses with volume from 200 to 450 $cm^3$ were used. According to the present invention recoveries for PCBs, organochlorine compounds assessed with the spiked prostheses depending on the compound, PBDEs and other compounds were all acceptable.

PCB masses in blank prostheses were low and varied between 0.3 and 3.4 ng per prosthesis depending on the congener. Concentrations of DDT compounds and its metabolites were below limits of detection in blank samples while blank levels of hexachlorobenzene were at worse just over 10% of those measured in exposed prostheses. For most PBDEs, levels found in blank prostheses were below limits of detection with these ranging from 0.2 to 0.7 ng per sample depending on the congener. BDE-99, BDE-153 and BDE-138 congeners were found at concentrations a factor of 2 to 20 above limits of detection.

Most organochlorine compounds and PCBs were found in exposed prostheses at levels well above those in blank prostheses. Masses of CB-118, CB-138, CB153, CB156 and p,p'-DDE found in exposed prostheses were between 10 and 1000× higher than blanks concentrations or limits of detection. Levels of other organochlorines and PCBs in exposed prostheses with lowest levels of contamination were at least 2-10× above prosthesis blank levels or limits of detection. The insecticide p,p'-DDT and its metabolite p,p'-DDE were both consistently measured above limits of detection in exposed prostheses.

Only BDE congeners 28, 47, 154 and 153 were consistently found in all exposed prostheses. Other congeners were found more sporadically, however these tended to be detected in samples where PCB and organ chlorine concentrations were highest (for samples 6 and 8 in Table 1). PBDE concentrations in exposed prostheses were between 1 and 30× limits of detection or levels in blanks.

Based on the relatively high diffusivity of contaminants such as PCBs observed in silicone polymer and low lipid-silicone partition coefficients, $K_{lip-sil}$, concentrations in newly inserted silicone prostheses are assumed to equilibrate with the body relatively rapidly.

The analysis of duplicate explanted prostheses can be very informative. The degree of agreement between contaminant concentrations in replicate prostheses is indicative of the repeatability of not only the analytical procedure in the laboratory but also of the sampling step. This sampling step includes the production of the silicone prostheses and all artefacts that can influence during exposure the final contaminant concentration in the prosthesis. The measurement of similar concentrations in intact duplicate samples would support the suggestion that lipophilic organic pollutant concentration/activity in various organs, fluids and tissues are at equilibrium in the body. Differences between two independent measurements in the body amounting to not much more than the analytical uncertainty would support it and would support the equilibrium sampling nature of the measurement.

In our study, mean concentrations and associated coefficients of variation were obtained for 2 sets of duplicate samples (samples 2, 6, 9 and 13 in Table 1) and data are presented in Table 2.

Matrices such as blood serum, adipose tissues or milk are commonly used for the bio monitoring of POPs in humans. Blood or milk samples are easier to collect than adipose tissues. Adipose tissue concentrations, however, are expected to provide a better measure of equilibrium concentrations since intra-individual variations concentrations measured in blood can be expected from for example changes in lipid levels with feeding/fasting. Because of differences in relative levels and types of lipids such as triglycerol, cholesterol or phospholipids between individuals and intra/inter-individual differences in contaminant metabolism, distribution and elimination, comparisons of blood and adipose tissue levels even on a normalised-lipid weight basis are complex.

The representativeness and suitability of POP concentrations measured in explanted silicone prostheses can be evaluated through comparison with literature data on POP levels measured in breast milk or blood serum from Norwegian women. Using seal oil lipid-to-silicone partition coefficients, $K_{lip-sil}$ for PCBs and DDTs, estimates of POP concentrations in lipids of participants of the present invention were calculated. This approach assumes that the influence of the type of silicone and of lipids on lipid-silicone partition coefficients is minor.

Silicone prostheses were obtained following breast implant surgery during a period spanning from July 2010 to January 2012. Reasons for explanation ranged from severe capsular contracture to a wish for a change in prosthesis size.

Prostheses were collected during surgical explanation from patients and wrapped individually in clean aluminium foil and stored in labelled plastic bags.

As soon as possible after, samples were stored in a freezer. Samples were then transported on ice to the laboratory and stored at −20° C. until analysis. For this proof-of-concept study, 9 prostheses were extracted and analysed. As shown in Table 1, these were selected to cover a range of prosthesis size, exposure time and manufacturer, as well as patient age and BMI (body mass index) index. Two prostheses were duplicates and their analysis aimed to investigate the reproducibility of the analytical steps as well as of the representativeness of the sampling (samples 2, 6, and 9 in Table 1). All prostheses were made of medical silicone gel enclosed in an outer silicone shell filled with gel with various degree of cohesiveness. Differences between prostheses from various producers include volume, type of silicone material, surface texture and thickness of the outer shell and cohesive degree of the filling gel. Prostheses were tinted and tinting from light yellow to orange appeared (from visual inspection only) dependent on exposure time.

Prostheses were placed in a pocket either sub glandular, i.e. under the breast gland, or sub muscular, i.e. partly under the great pectoralis muscle. Following implantation, connective tissues, i.e. collagen develop around the prosthesis to form a capsule.

Silicone prosthesis extraction were performed in batches of 10-12 samples and included a blank prosthesis (volume of 200-450 cm$^3$), a spiked prosthesis to assess extraction efficiency and a solvent blank to evaluate potential contamination during extraction and extract clean-up. Extraction of the whole prostheses was undertaken in pre-baked 2 L beakers kept in the dark to prevent photo degradation. Samples were brought to room temperature and the surface was rinsed with ultrapure water and dried with a clean tissue. Connective tissue capsule attached to the surface of prostheses were removed. Samples were extracted by soaking in 1 L of acetone for 24 hours. Acetone was chosen for its low capacity to swell the silicone matrix and because of the ease with which it can volatilise. Recovery standards for organochlorines, PCBs and PBDEs (including for BDE-209) were added to the acetone. It was expected that 24 hours is sufficient for chemicals (present in either phases) to partition between the solvent phase and the silicone prosthesis. The acetone was replaced by another 1 L of acetone and samples were extracted for a further 24 hours. The two volumes of acetone were combined and reduced under a gentle stream of nitrogen. Prostheses were weighed before and after solvent extraction to determine the total amount of silicone oils and other substances removed from the matrix during solvent extraction. A second set of internal standards was used to evaluate possible losses during the sample clean-up step. The solvent was changed to isohexane and sample clean-up consisted of repeated sulphuric acid treatment until no colouring of the extract could be observed. Extract were then passed through a silica-filled solid phase extraction column and eluted with dichloromethane or isohexane. Extracts were reduced to an adequate volume before analysis.

Analysis for o,p'-DDD, p,p'-DDD, o,p'-DDE, p,p'-DDD, o,p'-DDT, p,p'-DDT, hexachlorobenzene, octachlorostyrene, pentachlorobenzene, and PCB congeners 31/28 (co-eluting), 52, 101, 118, 153, 105, 138, 156, 180 and 209 was on a Agilent 7890A gas chromatographer (GC) linked to an Agilent 5975c inert XL EI/CI mass spectrometric (MS) detector operated in single ion monitoring mode (SIM) with electron impact ionisation (70 keV). Analytes were separated on a 30 m-long DB-5MS column (0.25 mm i.d. and 0.25 μm film thickness, Agilent JW Scientific, Santa Clara, USA) following 1 μL pulsed splitless injection (pulse pressure 20 psi for 1.2 min, injector temperature of 300° C.). The helium gas flow was set to 1.2 mL min$^{-1}$ and the GC oven temperature programme consisted of a step at 60° C. (held for 2 min) before an increase to 250° C. (at the rate 7° C. min$^{-1}$) and a final increase to 310° C. (at the rate of 15° C. min$^{-1}$) with this temperature held constant for a further 5 min. Ion source, quadrupole and transfer line temperatures were set to 230, 150 and 280° C., respectively. Quantification was performed using the relative response of surrogate internal standards (CB-30, CB-53 and CB-204) and 7-point calibration curves. Deviation (<20%) of the qualifier ion response relative to that of the quantifier ion was used for identification.

Analysis for polybrominated diphenyl ether congeners 28, 49, 71, 47, 66, 77, 100, 99, 85, 154, 153, 138 183, 196, 205 and 209 was on a Hewlett Packard 6890Plus GC coupled to a Hewlett Packard 5973 MS detector operated in negative chemical ionisation (with methane) and SIM mode. A pulsed splitless injection (4 μL, injector temperature of 280° C. and a pulse pressure of 50 psi held for 2 min) was used to transfer analytes onto a 15 m DB-5MS (0.25 mm i.d., 0.1 μm film thickness). The initial oven temperature was set to 120° C. held for 2 min before being increased to 345° C. at the rate of 25° C. min$^{-1}$ and held for a further 5 min. The helium gas flow was set to 1 mL min$^{-1}$ for the first 13 min and increased to 1.4 mL min$^{-1}$ at the rate of 0.1 mL min$^{-1}$ (held for a further 8 min). Temperatures of the ion source, quadrupole and transfer line were 250, 150 and 325° C., respectively. Ion fragments m/z 79 and 81 were used for qualifying and quantifying PBDEs while m/z 486.2, 488.2, 492.2 and 494.2 were also used for BDE-209. Internal standards used for PBDEs were $^{13}$C-BDE-119, BDE-181 and BDE-209.

Since prostheses were weighted before and after extraction, it was possible to estimate the total amount of substances and silicone oils that were concomitantly extracted from the prostheses with acetone. On average, 1.55% (w/w) of substances was removed from the prostheses.

TABLE 1

Sample characteristics including prosthesis brand, volume and exposure length and age and body mass index (BMI) of the female patients.

| Sample | Prosthesis Brand/Manufacturer | Volume (cm$^3$) | Exposure (yr) | Patient Age[a] | BMI[b] |
|---|---|---|---|---|---|
| 1 | Eurosilicone cristalline paragel | 260 | 4.1 | 38 | 24.2 |
| 2 (D)[c] | Silimed | 215 | 6.8 | 25 | 22.0 |
| 3 | Eurosilicone | 260 | 3.0 | 40 | 17.2 |
| 4 | Eurosilicone | 350 | 1.1 | 38 | 20.3 |
| 5 | —[d] | 180 | 20.3 | 45 | 19.0 |
| 6 (D)[c] | McGhan | 180 | 5.7 | 28 | 22.0 |
| 7 | McGhan | 180 | 15.0 | 41 | 25.4 |
| 8 | —[d] | 300 | 24.6 | 49 | 18.5 |

[a]patient age at the time of prosthesis removal;
[b]Body Mass Index;
[c]duplicates analysed;
[d]not known;
[e]two prostheses from different brands, with similar volumes and slight different exposure lengths

TABLE 2

Contaminant masses (ng sample$^{-1}$) in a set of duplicate prostheses with coefficients of variations (%).

| | Prosthesis contaminant mass (ng sample$^{-1}$) Sample 2[a] | |
|---|---|---|
| Analyte | Mean | CV[d] (%) |
| PeCB[e] | 5.6 | 22 |
| HCB[f] | 181 | 2.4 |
| CB-31/28 | 9.1 | 16 |
| OCS[g] | 3.5 | 6.6 |
| CB-101 | 7.6 | 27 |
| CB-118 | 52 | 2.4 |
| CB-153 | 252 | 1.0 |
| CB-105 | 11 | 7.4 |
| CB-138 | 123 | 4.4 |
| CB-156 | 15 | 19 |
| CB-180 | 9.3 | 179 |
| p,p'-DDE | 543 | 1.0 |
| p,p'-DDT | 38 | 14.6 |
| BDE-28 | 0.5 | 6.1 |
| BDE-47 | 1.6 | 88 |
| BDE-77 | 0.8 | |
| BDE-154 | 0.5 | 23 |
| BDE-153 | 3.7 | 0.3 |
| BDE-209 | 6.5 | |

[a]duplicates analysed in the same batch
[d]CV: coefficient of variation calculated from duplicate samples;
[e]PeCB: pentachlorobenzene;
[f]HCB: hexachlorobenzene;
[g]OCS: octachlorostyrene

TABLE 3

POP concentration in lipids estimated from concentrations measured in prostheses and lipid-normalised literature data for serum and milk from Norwegian studies.

| Analyte | $K_{lip-sil}$[a] (g g$^{-1}$) | Estimated $C_{lipid}$ (ng g$^{-1}$)[b] | Measured $C_{serum}$ (ng g$^{-1}$ lipid)[c] | Measured $C_{milk}$ (ng g$^{-1}$ lipid) |
|---|---|---|---|---|
| HCB[d] | 14.9 | 10.9 | | 11[e] |
| CB-31/28 | 19 | | | |
| CB-52 | 19.2 | | | |
| CB-101 | 26.3 | 0.5 | 5.8 | 6.4 (1.8-36)[f] |
| CB-118 | 35.2 | 7.5 | 8.0 | 9.3 (4.0-15)[f] |
| CB-153 | 38.1 | 62 | 43 | 38 (20-68) |
| CB-105 | 35.4 | 1.5 | | 1.8 (0.89-3.2)[f] |
| CB-138 | 34.0 | 27 | 20 | 16 (8-30)[f] |
| CB-156 | 50.8 | 4.5 | | 3.2 (1.5-5.9)[f] |
| CB-180 | 49.4 | 4.2 | 34 | 17 (8.5-32)[f] |
| o,p'-DDT | 21.3 | 0.8 | | |
| p,p'-DDT | 50.7 | 5.7 | | |

[a]Lipid-silicone partition coefficient for seal lipids taken from Jahnke et al. (2008);
[b]Lipid concentration estimated from silicone prosthesis concentrations, a silicone density of 1.0 and $K_{lip-sil}$ values from Jahnke et al. (2008). Estimates are given only for compounds for which $K_{lip-sil}$ values are available;
[c]Mean lipid-normalised serum concentration from Thomsen et al. (2007) for Norwegian women (n = 20) age 25-59 years old;
[d]HCB: hexachlorobenzene;
[e]Mean lipid-normalised concentrations for milk from Norwegian women (n = 377) from Polder et al. (2009);
[f]Lipid-normalised concentrations (median with range in brackets) for milk from Norwegian women (n = 70) from Thomsen et al. (2011).

In another embodiment an adhesive sorption material is placed on the surface of a contaminated area of the body. After a certain period of time the sorption material is removed from the host body. This result in detoxification of the body. An estimate of the concentration of toxic compounds present in a host body can be achieved by bringing the sorption material in contact with at least one solvent, and analyzing the extracted compounds.

Having described preferred embodiments of the invention it will be apparent to those skilled in the art that other embodiments incorporating the concepts may be used. These and other examples of the invention illustrated above are intended by way of example only and the actual scope of the invention is to be determined from the following claims.

REFERENCES

Jahnke A, McLachlan M S, Mayer P. Equilibrium sampling: Partitioning of organochlorine compounds from lipids into polydimethylsiloxane. Chemosphere 2008; 73: 1575-1581.

Polder A, Skaare J U, Skjerve E, Loken K B, Eggesbo M. Levels of chlorinated pesticides and polychlorinated biphenyls in Norwegian breast milk (2002-2006), and factors that may predict the level of contamination. Science of the Total Environment 2009; 407: 4584-4590.

Thomsen C, Liane V H, Becher G. Automated solid-phase extraction for the determination of polybrominated diphenyl ethers and polychlorinated biphenyls in serum—application on archived Norwegian samples from 1977 to 2003. Journal of Chromatography B-Analytical Technologies in the Biomedical and Life Sciences 2007; 846: 252-263.

Thomsen C, Haug L S, Stigum H, Froshaug M, Broadwell S L, Becher G. Changes in Concentrations of Perfluorinated Compounds, Polybrominated Diphenyl Ethers and Polychlorinated Biphenyls in Norwegian Breast-Milk during Twelve Months of Lactation (vol 44, pg 9550, 2010). Environmental Science & Technology 2011; 45: 3192-3192.

The invention claimed is:

1. A method for detoxification of at least one compound or fluid in a host body, the method comprising:
providing a sorption material having at least one phase, where sorption of said at least one compound or fluid in at least one phase of said sorption material is effected, wherein said sorption material is
an implant, a breast implant or prosthesis which previously has been implanted in a host body for a certain period of time, or
an adhesive sorption material which previously has been present on the surface of a host body for a certain period of time;
inserting the sorption material in the host body for a certain period of time, wherein during the certain period of time, the sorption material absorbs a portion of the at least one compound; and
removing the sorption material from the host body after the certain period of time to thereby achieve detoxification.

2. The method according to claim 1, wherein said sorption material comprises at least one phase comprising at least one of the following: gels, polymers, polydimethylsiloxane, Ethylene Vinyl Acetate, biocompatible and medical grade polymers, rubbery polymers, silicone, additives such as activated carbon, resins, molecularly imprinted polymer (MIPs), nanoparticles, nanomaterials, chelating agents.

3. The method according to claim 1, wherein the sorption material possesses the ability of sorption of at least one of the following compounds: any organic molecule, any inorganic molecule or organ metallic molecule.

4. The method according to claim 3, wherein the sorption material possesses the ability of sorption of at least one hydrophobic compound or fluid.

5. The method according to claim 3, wherein the sorption material possesses the ability of sorption of methyl mercury.

6. The method according to claim 3, wherein the sorption material possesses the ability of sorption of radionuclides.

7. The method according to claim 3, wherein the sorption material possesses the ability of sorption of any neutral non-ionised substances with an octanol-water partition coefficient (log $K_{ow}$)>3.

8. The method according to claim 3, wherein the sorption material possesses the ability of sorption of at least one of the following compounds: dichlorodiphenyltrichloroethane isomers (DDT) and metabolites, hexachlorobenzene (HCB), octachlorostyrene (OCS), pentachlorobenzene (PeCB), polychlorinated biphenyl congeners (209 PCB congeners) and brominated diphenyl ethers (209 PBDE congeners), nonpolar degradation products thereof such as hydroxyl-BDEs, polycyclic aromatic hydrocarbons and metabolites thereof, metabolites of PCBs/PBDEs, hexabromocyclododecane.

9. A method for removal of at least one compound or fluid in a host body, the method comprising:
providing a sorption material having at least one phase, where sorption of said at least one compound or fluid in at least one phase of said sorption material is effected, wherein said sorption material is
an implant or prosthesis which previously has been implanted in a host body for a certain period of time, or
an adhesive sorption material which previously has been present on the surface of a host body for a certain period of time,
inserting the sorption material in the host body for a certain period of time, wherein during the certain period of time, the sorption material absorbs a portion of the at least one compound; and
removing the sorption material from the host body after the certain period of time to thereby remove the portion of the at least one compound.

10. The method according to any of claim 9, wherein said sorption material comprises at least one phase comprising at least one of the following: gels, polymers, polydimethylsiloxane, Ethylene Vinyl Acetate, biocompatible and medical grade polymers, rubbery polymers, silicone, additives such as activated carbon, resins, molecularly imprinted polymer (MIPs), nanoparticles, nanomaterials, chelating agents.

11. The method according to claim 9, wherein the sorption material possesses the ability of sorption of at least one of the following compounds: any organic molecule, any inorganic molecule or organ metallic molecule.

12. A method for determining a concentration of at least one compound or fluid in a host body, the method comprising:
providing a sorption material having at least one phase, where sorption of said at least one compound or fluid in at least one phase of said sorption material is effected and the content of the at least one compound or fluid in said sorption material is analysed, wherein the sorption material is an implant or a prosthesis and/or an adhesive bandage which has been implanted in a host body or has been present on the surface of a host body for a certain period of time;
inserting the sorption material in the host body for a certain period of time, wherein during the certain period of time, the sorption material adsorbs or absorbs a portion of the at least one compound, wherein said certain period of time comprises at least one of the following: 3-5 days, 6-10 days, 1 month, 2 months, 3-6 months, 7-12 months, 18 months, 2-5 years, 6-10 years, 11-15 years, 16-20 years, 21-30 years, 31-40 years;
removing the sorption material from the host body after the certain period of time; and
measuring a quantity of the at least one compound adsorbs or absorbs by the sorption material.

13. The method according to claim 12, for providing an estimate of the concentration of said compound(s) present in a host body in which the sorption material previously has been implanted for a certain period of time, said method comprising the following steps:

bringing said sorption material in contact with at least one solvent, analyzing extracted compounds.

14. The method according to claim 13, wherein an acid clean-up is performed optionally prior to analyzing the extracted compounds.

15. The method according to claim 14, wherein the sorption material after being brought in contact with at least one solvent is brought to a temperature in at least one of the selected ranges: −10° C. to +10° C., −5° C. to 5° C., −5° C. to 0° C., 0° C. to 5° C.

16. The method according to claim 13, wherein the sorption material after being brought in contact with at least one solvent is brought to a temperature in at least one of the selected ranges: −10° C. to +10° C., −5° C. to 5° C., −5° C. to 0° C., 0° C. to 5° C.

17. The method according to claim 13, wherein the extracted compounds are analyzed using one of the following methods: gas chromatography, liquid chromatography or mass spectrometric methods for detection and quantification.

18. The method according to any of claim 12, wherein said sorption material comprises at least one phase comprising at least one of the following: gels, polymers, polydimethylsiloxane, Ethylene Vinyl Acetate, biocompatible and medical grade polymers, rubbery polymers, silicone, additives such as activated carbon, resins, molecularly imprinted polymer (MIPs), nanoparticles, nanomaterials, chelating agents.

19. The method according to claim 12, wherein the sorption material possesses the ability of sorption of at least one of the following compounds: any organic molecule, any inorganic molecule or organ metallic molecule.

* * * * *